US009937279B2

(12) United States Patent
Beniash et al.

(10) Patent No.: US 9,937,279 B2
(45) Date of Patent: *Apr. 10, 2018

(54) BONE SUBSTITUTE NANOCOMPOSITES AND METHODS OF SYNTHESIS USING MULTIPHOSPHORYLATED PEPTIDES

(71) Applicant: UNIVERSITY OF PITTSBURGH—OF THE COMMONWEALTH SYSTEM OF HIGHER EDUCATION, Pittsburgh, PA (US)

(72) Inventors: Elia Beniash, Pittsburgh, PA (US); Charles S. Sfeir, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/943,479

(22) Filed: Nov. 17, 2015

(65) Prior Publication Data
US 2016/0067376 A1  Mar. 10, 2016

Related U.S. Application Data

(62) Division of application No. 14/079,086, filed on Nov. 13, 2013, now Pat. No. 9,221,888.

(60) Provisional application No. 61/725,796, filed on Nov. 13, 2012.

(51) Int. Cl.
| | |
|---|---|
| A61K 38/10 | (2006.01) |
| A61K 38/16 | (2006.01) |
| C01F 5/00 | (2006.01) |
| A61L 27/28 | (2006.01) |
| A61L 27/22 | (2006.01) |
| C07K 14/47 | (2006.01) |
| C07K 7/08 | (2006.01) |
| A61L 27/46 | (2006.01) |
| A61L 27/54 | (2006.01) |
| A61L 27/24 | (2006.01) |
| A61L 27/48 | (2006.01) |
| C07K 14/00 | (2006.01) |
| A61K 38/00 | (2006.01) |

(52) U.S. Cl.
CPC ............ *A61L 27/227* (2013.01); *A61L 27/24* (2013.01); *A61L 27/46* (2013.01); *A61L 27/48* (2013.01); *A61L 27/54* (2013.01); *C07K 7/08* (2013.01); *C07K 14/001* (2013.01); *C07K 14/47* (2013.01); *A61K 38/00* (2013.01); *A61L 2300/25* (2013.01); *A61L 2300/252* (2013.01); *A61L 2430/02* (2013.01)

(58) Field of Classification Search
None
See application file for complete search history.

(56) References Cited

U.S. PATENT DOCUMENTS

| 7,846,445 | B2 | 12/2010 | Schellenberger et al. |
| 7,855,279 | B2 | 12/2010 | Schellenberger et al. |
| 8,492,530 | B2 | 7/2013 | Schellenberger et al. |
| 9,221,888 | B2* | 12/2015 | Beniash ................. A61L 27/46 |
| 9,469,677 | B2* | 10/2016 | Beniash ................. C07K 14/47 |
| 2007/0087959 | A1 | 4/2007 | Sfeir et al. |
| 2008/0039341 | A1 | 2/2008 | Schellenberger et al. |
| 2009/0098050 | A1 | 4/2009 | Yarbrough et al. |

OTHER PUBLICATIONS

George et al., "The Carboxyl-terminal Domain of Phosphophoryn Contains Unique Extended Triplet Amino Acid Repeat Sequences Forming Ordered Carboxyl-Phosphate Interaction Ridges That May Be Essential in the Biomineralization Process", The Journal of Biological Chemistry, 1996, pp. 32869-32873, vol. 271, No. 53, Issue of Dec. 20.
Ritchie et al., "A novel rat 523 amino acid phosphophoryn: nucleotide sequence and genomic organization 1", Biochimica et Biophysica Acta 1520 (2001) 212-222, Published 2001 Elsevier Science B.V.
Deshpande et al., "Primary Structure and Phosphorylation of Dentin Matrix Protein 1 (DMP1) and Dentin Phosphophoryn (DPP) Uniquely Determine Their Role in Biomineralization", Biomacromolecules, 2011 American Chemical Society, pp. 2933-2945, ACS Publications.
Sfeir et al., "Synthesis of bone-like nanocomposites using multiphosphorylated peptides", Acta Biomaterials 10 (2014) pp. 2241-2249, 2014 Acta Materialia Inc., Published by Elsevier Ltd.

* cited by examiner

*Primary Examiner* — Elizabeth C. Kemmerer
(74) *Attorney, Agent, or Firm* — Eckert Seamans Cherin & Mellott, LLC; Carol A. Marmo

(57) ABSTRACT

The invention relates to peptides including DEDE (SSD)$_n$DEG indicated by SEQ NO. 1, RRRDEDE (SSD)$_n$DEG indicated by SEQ NO. 2, RRRGDEDE (SSD)$_n$DEG indicated by SEQ NO. 3, and LKKLKKLD-EDE(SSD)nDEG indicated by SEQ NO. 4, wherein n is an integer from 2 to 20. The invention also relates to phosphorylating these peptides at multiple amino acid sites by employing casein kinases. These phosphorylated peptides may be used in various applications such as forming mineralized collagen fibrils and biomimetic composites for use in tissue repair and regeneration.

10 Claims, 13 Drawing Sheets

CK1

1    4    24   Hours

CK2

1    4    24   Hours

CK1+CK2

1    4    24   Hours

```
                        SEQUENCE LISTING

<160> NUMBER OF SEQ ID NOS: 4

<210> SEQ ID NO 1
<211> LENGTH: 67
<212> TYPE: PRT
<213> ORGANISM: Artificial
<220> FEATURE:
<223> OTHER INFORMATION: derived from consensus mammalian sequence of
      DSPP
<220> FEATURE:
<221> NAME/KEY: MISC_FEATURE
<222> LOCATION: (5)..(64)
<223> OTHER INFORMATION: [Ser Ser Asp] repeats (n varies from 2 to 20)
<220> FEATURE:
<221> NAME/KEY: MISC_FEATURE
<222> LOCATION: (1)..(4)
<223> OTHER INFORMATION: Casein kinase 1 recognition motif
<220> FEATURE:
<221> NAME/KEY: MISC_FEATURE
<222> LOCATION: (65)..(67)
<223> OTHER INFORMATION: Casein kinase 2 recognition motif

<400> SEQUENCE: 1

Asp Glu Asp Glu Ser Ser Asp Ser Ser Asp Ser Ser Asp Ser Ser Asp
1               5                   10                  15

Ser Ser Asp Ser Ser Asp Ser Ser Asp Ser Ser Asp Ser Ser Asp Ser
                20                  25                  30

Ser Asp Ser Ser Asp Ser Ser Asp Ser Ser Asp Ser Ser Asp Ser Ser
            35                  40                  45

Asp Ser Ser Asp Ser Ser Asp Ser Ser Asp Ser Ser Asp Ser Ser Asp
        50                  55                  60

Asp Glu Gly
65

<210> SEQ ID NO 2
<211> LENGTH: 70
<212> TYPE: PRT
<213> ORGANISM: Artificial
<220> FEATURE:
<223> OTHER INFORMATION: derived from consensus mammalian sequence of
      DSPP
<220> FEATURE:
<221> NAME/KEY: MISC_FEATURE
<222> LOCATION: (8)..(68)
<223> OTHER INFORMATION: [Asp Ser Ser] repeats (n varies from 2 to 20)
```

```
<220> FEATURE:
<221> NAME/KEY: MISC_FEATURE
<222> LOCATION: (1)..(3)
<223> OTHER INFORMATION: Insertion of 3 Arg at the N terminus of the
      peptide
<220> FEATURE:
<221> NAME/KEY: MISC_FEATURE
<222> LOCATION: (4)..(7)
<223> OTHER INFORMATION: Casein kinase 1 recognition motif
<220> FEATURE:
<221> NAME/KEY: MISC_FEATURE
<222> LOCATION: (69)..(71)
<223> OTHER INFORMATION: Casein kinase 2 recognition motif

<400> SEQUENCE: 2

Arg Arg Arg Asp Glu Asp Glu Ser Ser Asp Ser Ser Asp Ser Ser Asp
1               5                   10                  15

Ser Ser Asp Ser Ser Asp Ser Ser Asp Ser Ser Asp Ser Ser Asp Ser
            20                  25                  30

Ser Asp Ser Ser Asp Ser Ser Asp Ser Ser Asp Ser Ser Asp Ser Ser
        35                  40                  45

Asp Ser Ser Asp Ser Ser Asp Ser Ser Asp Ser Ser Asp Ser Ser Asp
    50                  55                  60

Ser Ser Asp Asp Glu Gly
65                  70

<210> SEQ ID NO 3
<211> LENGTH: 71
<212> TYPE: PRT
<213> ORGANISM: Artificial
<220> FEATURE:
<223> OTHER INFORMATION: derived from consensus mammalian sequence of
      DSPP
<220> FEATURE:
<221> NAME/KEY: MISC_FEATURE
<222> LOCATION: (9)..(69)
<223> OTHER INFORMATION: [Asp Ser Ser] repeats (n varies from 2 to 20)
<220> FEATURE:
<221> NAME/KEY: MISC_FEATURE
<222> LOCATION: (1)..(3)
<223> OTHER INFORMATION: Insertion of 3 Arg at the N terminus of the
      peptide
<220> FEATURE:
<221> NAME/KEY: MISC_FEATURE
<222> LOCATION: (4)..(4)
<223> OTHER INFORMATION: Insertion of Gly to generate an Arg Gly Asp
      integrin recognition motif. Other signalling motifs, such as IKVAV
      can be inserted into the sequence
<220> FEATURE:
<221> NAME/KEY: MISC_FEATURE
<222> LOCATION: (5)..(8)
<223> OTHER INFORMATION: Casein kinase 1 recognition motif
<220> FEATURE:
<221> NAME/KEY: MISC_FEATURE
<222> LOCATION: (70)..(73)
<223> OTHER INFORMATION: Casein kinase 2 recognition motif

<400> SEQUENCE: 3

Arg Arg Arg Gly Asp Glu Asp Glu Ser Ser Asp Ser Ser Asp Ser Ser
1               5                   10                  15

Asp Ser Ser Asp Ser Ser Asp Ser Ser Asp Ser Ser Asp Ser Ser Asp
            20                  25                  30

Ser Ser Asp Ser Ser Asp Ser Ser Asp Ser Ser Asp Ser Ser Asp Ser
        35                  40                  45

Ser Asp Ser Ser Asp Ser Ser Asp Ser Ser Asp Ser Ser Asp Ser Ser
    50                  55                  60

Asp Ser Ser Asp Asp Glu Gly
65                  70
```

```
<210> SEQ ID NO 4
<211> LENGTH: 74
<212> TYPE: PRT
<213> ORGANISM: Artificial
<220> FEATURE:
<223> OTHER INFORMATION: derived from consensus mammalian sequence of
      DSPP
<220> FEATURE:
<221> NAME/KEY: MISC_FEATURE
<222> LOCATION: (12)..(72)
<223> OTHER INFORMATION: [Asp Ser Ser] repeats (n varies from 2 to 20)
<220> FEATURE:
<221> NAME/KEY: MISC_FEATURE
<222> LOCATION: (8)..(11)
<223> OTHER INFORMATION: Casein kinase 1 recognition motif
<220> FEATURE:
<221> NAME/KEY: MISC_FEATURE
<222> LOCATION: (73)..(75)
<223> OTHER INFORMATION: Casein kinase 2 recognition motif
<220> FEATURE:
<221> NAME/KEY: MISC_FEATURE
<222> LOCATION: (1)..(7)
<223> OTHER INFORMATION: Leucine zipper motif

<400> SEQUENCE: 4

Leu Lys Lys Leu Lys Lys Leu Asp Glu Asp Glu Ser Ser Asp Ser Ser
1               5                   10                  15

Asp Ser Ser Asp Ser Ser Asp Ser Ser Asp Ser Ser Asp Ser Ser Asp
            20                  25                  30

Ser Ser Asp Ser Ser Asp Ser Ser Asp Ser Ser Asp Ser Ser Asp Ser
            35                  40                  45

Ser Asp Ser Ser Asp Ser Ser Asp Ser Ser Asp Ser Ser Asp Ser Ser
    50                  55                  60

Asp Ser Ser Asp Ser Ser Asp Asp Glu Gly
65                  70
```

BONE SUBSTITUTE NANOCOMPOSITES AND METHODS OF SYNTHESIS USING MULTIPHOSPHORYLATED PEPTIDES

This application is a Divisional Patent Application of U.S. patent application Ser. No. 14/079,086, issued as U.S. Pat. No. 9,221,888 on Dec. 29, 2015, entitled "Bone Substitute Nanocomposites and Methods of Synthesis Using Multiphosphorylated Peptides" and filed on Nov. 13, 2013, which claims priority under 35 U.S.C. § 119(e) from U.S. Provisional Patent Application No. 61/725,796, entitled "Bone Substitute Nanocomposites and Methods of Synthesis Using Multiphosphorylated Peptides" and filed on Nov. 13, 2012, the contents of which are incorporated herein by reference.

This invention was made with government support under DE 106703 and DE 016123 awarded by the National Institutes of Health (NIH). The government has certain rights in the invention.

BACKGROUND OF THE INVENTION

1. Field of the Invention

This invention relates to biomimetic composites having integrated organic and inorganic phases, methods of synthesis for producing the biomimetic composites, and use in biomimetic nanostructured materials for repair and regeneration of mineralized tissue.

2. Background Information

Two examples of mineralized tissue include bone and dentin. Both of these are highly organized hierarchical nanocomposites in which mineral and organic phases interface at a molecular level. There are materials known in the art for use in repairing mineralized tissue. However, there are disadvantages associated with these known materials. For instance, there are known graft materials consisting of ceramic powders or physical blends of mineral and organic phases. These materials have been found to exhibit mechanical properties significantly inferior to those of actual mineralized tissue.

Mineralized tissues, such as bone and dentin are unique, hierarchical nanocomposites which can include about 70% by weight carbonated apatite, 20-25% by weight organic matrix, and 5-10% by weight water. Mineralized collagen fibrils are the major organic component of these tissues. Other non-collagenous proteins (NCPs) and glycoproteins account for less than about 10% of the total organic content and contribute to the regulation of mineralization, cell signaling and mechanical performance of the tissue.

Thus, the basic building blocks of bone and dentin are mineralized collagen fibrils, which are the first level of structural hierarchy of these tissues. Mineralized collagen fibrils contain stacks of plate-shaped crystallites of carbonated apatite. These crystallites can be about 3-5 nm thick, about 50 to 100 nm in two other dimensions, and aligned with their crystallographic c-axes along a fibril axis. It has been shown that the mineral component in these fibrils has almost two times greater strain than geologic or synthetic apatite and the organic component is significantly stiffer than nonmineralized collagen. These differences may be due in part to one or more of the following: (i) the nanoscopic dimensions of the crystallites, (ii) the plate-like shape of the crystallites which leads to insensitivity of these nanocrystals to flaws, and (iii) extremely high surface-to-bulk ratio which translates into high strain values.

Furthermore, the interlaced structure of the mineralized collagen fibrils creates intimate interactions of the mineral crystallites with collagen triple helices resulting in an unique mineral-organic interface at the molecular level.

The mineralized tissues have a complex organization and unique mechanical properties. In contrast, known composite bone-grafting materials are simple physical blends of organic and mineral phases. Therefore, it is highly desirable to design novel nanomaterials in accordance with the structure and properties of the mineralized tissues.

NCPs are involved in collagen mineralization. A characteristic of NCPs is the disproportionately large percentage of acidic amino acids such as Asp, Glu and Ser$^{(P)}$. For example, the major NCP in dentin is phosphophoryn (DPP). DPP includes primarily Ser-Ser-Asp repeat motifs with more than 90% of serines phosphorylated. Protein phosphorylation is one of the most common post-translational modifications. However, the vast majority of phosphorylated proteins contain only a small amount of phosphorylation sites adjacent to kinase-specific recognition motifs. The precise phosphorylation mechanisms of the highly phosphorylated proteins from the mineralized tissues are not adequately understood in the art. It has been proposed that casein kinases (CK) 1 and 2 phosphorylate DPP intracellularly in the endoplasmic reticulum. According to certain hypotheses, phosphorylation occurs via a chain or hierarchical reaction wherein one phosphorylated serine becomes a part of the CK recognition site which leads to subsequent phosphorylation of new serines. CK transfer γ-phosphate of ATP (or GTP) to the hydroxyl group of serine or threonine, or to the phenolic hydroxyl on tyrosine residues in proteins.

A number of peptides mimicking NCPs have been synthesized. The synthesis included introducing phosphorylated amino acids during the synthesis phase. However, this approach for synthesis of bioinspired peptides has limitations. For example, introducing any single phosphorylated amino-acids during peptide synthesis leads to a significant decrease in yield, thereby limiting the total number of phosphorylated amino acids that can be added to a peptide.

SEQUENCE LISTING

Figure 1:
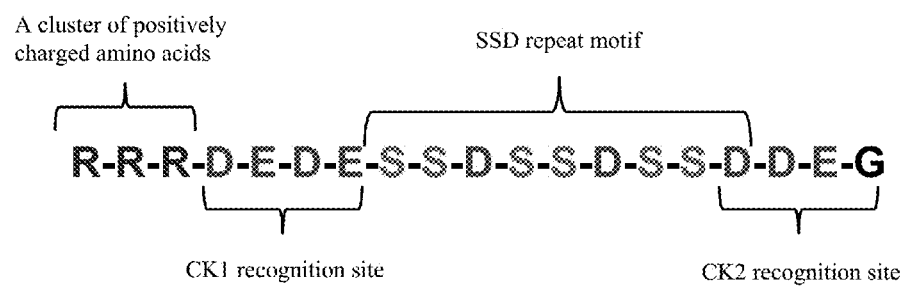
FIG. 1 is a peptide design schematic which shows a R-SSD$_3$ sequence containing: i) three Arg amino acids at its N-terminus end, ii) followed by four amino acids forming the CK1 recognition site and iii) three Ser-Ser-Asp repeats. CK2 recognition motif is located at the C-terminus end of the peptide. This peptide design schematic is in accordance with certain embodiments of the invention and is indicated by SEQ NO. 2.

The amino acid sequences listed in the accompanying sequence listing are shown using standard letter abbreviations and the sequence listing is incorporated by reference herein.

DETAILED DESCRIPTION OF THE INVENTION

The invention relates to synthesis of biomimetic composites (e.g., nanofibrils) with highly integrated organic and inorganic interfaces designed and developed in accordance with actual mineralized collagen fibrils (e.g., nanofibrils) of bone and dentin. Novel peptides including multiple serines, such as three Ser-Ser-Asp repeat motifs, are designed based on DPP which is a highly phosphorylated/multiphosphorylated protein found in dentin and alveolar bone. In certain embodiments, up to 80% of the serines in each of the peptides can be phosphorylated by casein kinases.

In certain embodiments, the peptides include the following:

1) DEDE(SSD)$_n$DEG, wherein n represents the number of SSD motifs and is an integer from 2 to 20, indicated by SEQ NO. 1;

2) RRRDEDE(SSD)$_n$DEG, wherein n represents the number of R-SSD motifs and is an integer from 2 to 20, indicated by SEQ NO. 2;

3) RRRGDEDE(SSD)$_n$DEG, wherein n represents the number of SSD motifs and is an integer from 2 to 20, indicated by SEQ NO. 3; and 4) LKKLKKLDEDE(SSD)$_n$DEG wherein n represents the number of SSD motifs and is an integer from 2 to 20, indicated by SEQ NO. 4.

Peptide 3) above contains the RGD motif for cell integrin binding. Functional bioactive peptide motifs other than RGD can be used. Peptide 4) above contains leucine zipper domains to promote self-assembly.

The peptides of the invention can induce biomimetic calcium phosphate mineralization of collagen fibrils. In the presence of these phosphorylated peptides, highly organized mineralized collagen fibrils structurally similar to the mineralized collagen fibrils of actual bone and dentin can be formed. Thus, DPP-inspired peptides can be used to synthesize highly organized biomimetic composite nanofibrils, with integrated organic and inorganic phases. These composites are integral in the development of biomimetic nanostructured materials for use in the repair and regeneration of mineralized tissue. These bioinspired peptides also have the ability to promote osteogenesis.

In certain embodiments, the bioinspired peptides include the following:

```
5) DEDESSDSSDSSDDEG (SSD₃)
   indicated by SEQ NO. 1;

6) RRRDEDESSDSSDSSDDEG (R-SSD₃)
   indicated by SEQ NO. 2;

7) RRRDEDESSDSSDSSDSSDDEG (R-SSD₅)
   indicated by SEQ NO. 2;
and

8) RRRGDEDESSDSSDSSDDEG (RGD-SSD₃)
   indicated by SEQ NO. 3.
```

In 8) above indicated by SEQ NO. 3 the RGD motif provides for integrin binding for better integration into living tissues. These peptides can be phosphorylated at multiple sites. Further, these peptides can include other signaling self-assembly or molecular recognition motifs.

It has been found that in the presence of two phosphorylated NCPs, such as DPP and dentin matrix protein 1 (DMP1), highly organized mineralized collagen fibrils which are similar to those found in bone and dentin can be formed. In contrast, in the presence of nonphosphorylated DPP and DMP1 no organized mineralization of collagen fibrils was observed. Thus it has been demonstrated that phosphorylation contributes to proper bone mineralization. The phosphorylated peptides of the invention can be employed for modeling NCPs for synthesis of bioinspired nanostructured materials based on mineralized collagen fibrils.

In accordance with the invention, mineralized collagen fibril is formed by employing fibril collagen, organized mineral crystals, and at least one of Peptides 1) through 8) indicated by SEQ NOS. 1-4 which promotes the organized mineralization of collagen fibrils.

Further, in accordance with the invention, a biomimetic composite is formed by employing fibril collagen, organized mineral crystals and at least one of Peptides 1) through 8) indicated by SEQ NOS. 1-4 which promotes the organized mineralization of collagen fibrils.

The invention includes post-synthesis phosphorylation by adapting biological phosphorylation strategies for highly phosphorylated NCPs in order to: i) determine the extent of phosphorylation of the NCPs, e.g., how highly phosphorylated NCPs are phosphorylated, and to assess hierarchical or chain phosphorylation in serine high-density sequences, thereby resulting in synthesis of phosphopeptides with multiple phosphate groups, and ii) assess the ability of highly phosphorylated bioinspired peptides to induce the organized mineralization of collagen fibrils for the development of bioinspired nanostructured hierarchical composites for mineralized tissue repair and regeneration.

EXAMPLES

Example 1—Peptide Synthesis

The designed peptide: RRRDEDESSDSSDSSDDEG (R-SSD₃) (molecular weight 2142.91 Da, at 92.26% purity)

indicated by SEQ NO. 2 was synthesized by 21$^{st}$ Century Biochemicals (Marlboro Mass.). The purity of the peptide was determined using mass spectrometry and HPLC prior to shipment.

Peptide Phosphorylation

Casein Kinase 1 active (CK1) (0.2 mg/ml), Casein Kinase 2 active (CK2), (0.1 mg/ml)Mg/ATP cocktail, and P81 phosphocellulose paper were obtained from Upstate Cell Signaling Solutions (Lake Placid, N.Y.). Assay Dilution Buffer I and CK2 substrate peptide (1 mM), and active CK1 (0.25 mg/ml) were obtained from Millipore (Billerica, Mass.). Adenosine 5'-triphosphate, Ultratide/Isobluestabilized (ATP γ-$^{32}$P) with a specific activity of 800 Ci/mmol was purchased from MP Biomedical (Solon, Ohio). 16.5% Tris-Tricine gel, 10× Tris-Tricine/SDS buffer, and Tricine sample buffer were purchased from Bio Rad Laboratories (Hercules, Calif.). ACS grade phosphoric acid (85%), ScintiVerse Scintanalyzer and acetone were purchased from Fisher Scientific (Pittsburgh, Pa.). Micro 1000 MWCO Tube-O-DIALYZER was purchased from G-Biosciences (St. Louis, Mo.).

R-SSD$_3$ indicated by SEQ NO. 2 was phosphorylated in vitro by CK1, CK2 or a mixture of both kinases. ATP was used as a source of phosphate; and [γ-$^{32}$P] ATP was used for the scintillation counter experiments. The standard assay mixture consisted of 50 mM Tris-HCl, pH 7.4, 5 mM MgCl$_2$, 1 mM EGTA and 10 mM β-glycerophosphate. The assay was carried out in a total volume of 40 µl, containing substrate peptide (10 µl of 1 mg/ml solution), 10 µl of Assay Dilution Buffer I (ADBI with a composition of 20 mM MOPS, pH 7.2, 25 mM β-glycerol phosphate, 5 mM EGTA, 1 mM sodium orthovanadate, 1 mM dithiothreitol) and 10 µl of active casein kinase (1 or 2). The samples were vortexed and kept for 20 minutes at room temperature before transferring into a water bath at 30° C. The reaction was started by adding 10 µl of ATP (cold Mg-ATP and 1 µCi of [γ-$^{32}$P] ATP) and the reaction mixture was incubated at 30° C. in a shaker for 1 hr. To assess the kinetics of the reactions, phosphorylation was allowed to proceed for 20 minutes, 1 hour, 4 hours and 24 hours before the reaction was stopped. The reaction was terminated by adding 40 µl of loading Tricine sample buffer (200 mM Tris-HCl, pH 6.8, 2% SDS, 40% glycerol, 0.04% Coomassie G-250 dye). The samples were then boiled in a water bath for five minutes and subjected to electrophoresis on 16.5% Tris-Tricine gel run using Tris-Tricine/SDS buffer (containing 100 mM Tris, 100 mM Tricine, 0.1% SDS, pH 8.3) at 100V for 1.5 hours.

For mass spectrometry (MS) analysis, the reaction was performed as above, however, radiolabeled ATP was not used and the reaction mixture was transferred into a Tube-O-DIALYZER with a MWCO of 1000 and dialyzed overnight.

Characterization of Phosphorylation

Recombinant casein kinase 1 (CK1; Cat #14-112) and casein kinase 2 (CK2; Cat #14-197) were obtained from Millipore Inc. ATP and [γ-$^{32}$P] ATP were obtained from Sigma-Aldrich (St. Louis, Mo.) and Perkin Elmer (Shelton, Conn.), respectively.

In vitro Phosphorylation Assay

In vitro phosphorylation assay was performed according to conventional procedure. 25 ul reactions containing 1 µg of R-SSD3 peptide indicated by SEQ NO. 2, in the presence and absence of 300 ng of either CK1 or CK2 or both containing 10 µCi $^{32}$P γ [ATP]. The reactions were performed in triplicate at 30° C. for 1 hour, 4 hours and 24 hours using one batch of radiolabeled ATP and enzymes from a single lot.

The reaction products were purified using SDS-PAGE, visualized by autoradiography, and band intensities were quantified using a Kodak 1D 3.6 imaging system. After autoradiography, the gel was overlaid on the autoradiogram, the individual protein bands were excised and $^{32}$P incorporation was determined using a liquid scintillation counter (Beckman LS6500 system). To calculate the number of moles of phosphates transferred to 1 ug of peptide (0.466 pM) in the kinase reaction, the mean counts per minute obtained in the kinase reactions from triplicates (minus blank) are divided by the specific activity of the $^{32}$Pγ[ATP] in the kinase assay, as follows.

Number of pM of $P$32 transferred/pM of peptide =
$$\frac{\text{Mean } CPM \text{ of phosphoryled peptides}}{\text{Specific activity of } 32P \text{ added in the kinase reaction}} \times \frac{1.00}{0.466}$$

MALDI-TOF MS and LC-ESI MS Analyses

For MALDI-TOF-MS analysis, the peptides and CHCA matrix (α-cyano-4-hydroxycinnamic acid, 10 µg/µl, in 50% acetonitrile containing 0.1% trifluoroacetic acid) solutions were premixed in a small Eppendorf tube, spun down and remixed three times, then applied directly to the sample plate. Once applied to the target, the sample was allowed to air dry. The samples were analyzed using an Applied Biosystems (Foster City, Calif.) Voyager DE Pro or 4700 Proteomics Analyzer TOF/TOF instrument. The samples were also analyzed by LC-MS/MS on a ThermoFischer (Waltham, Mass.) Surveyor LC System coupled to a ThermoFischer LCQ Deca XP Plus mass spectrometer equipped with a nanospray ion source and also a ThermoFischer LTQ-XL instrument. The LC System contained a sample trap followed by a C18 column (BioBasic C18 PicoFrit column, 10 cm×75 µM, New Objective, Inc., Woburn, Mass.). The elution gradient for chromatographic separation of the peptides was obtained with two solvents: solvent A (100% water with 0.1% formic acid) and solvent B (100% acetonitrile with 0.1% formic acid). The solvent gradient was increased from 5% to 50% solvent B over 25 minutes, further increased from 50% to 98% solvent B over 5 minutes, continued at 98% solvent B for 5 minutes, reduced from 98% to 5% solvent B over 5 minutes, then finished at 5% B for 10 minutes. The flow rate of the LC system was 160 nl/min.

Upon elution of the C18 column, the analyte was ionized by nano-capillary ESI. Ions were produced in positive mode (ESI voltage at 1.6 kV; heated capillary at 180° C.). A full MS scan was done (m/z 300-2000 AMU) followed by three MS/MS scans on the three most intense peaks with dynamic exclusion. The MS/MS spectra were analyzed with BioWorks 3.2 Browser with the Sequest search engine. The search used the UniProtKB/Swiss-Prot human protein knowledgebase, which was first indexed for a trypsin digest, no missed cleavages, and three modifications (oxidation of methionine, carboxyamidomethylation and methylation of cysteine). The search results that were accepted contained cross correlation scores (Xcorr) for singly charged peptides>1.5, doubly charged peptides>2.0, and triply charged peptides>3.0.

Mineralization Experiments

Mineralization experiments were carried out using a modification of an "on grid" mineralization setup developed in a lab and published in the art. The type I collagen fibrils were reconstituted on carbon-coated Cu grids, mesh #400

(EMS, Hatfield, Pa.) from an acidic rat tail collagen solution. Concentrated 10×PBS (mono- and disodium phosphate totaling 40 mM and 1.5 M NaCl), phosphorylated with CK2 and nonphosphorylated protein stock solution, deionized distilled water (DDW) and were mixed to obtain 4 mM PBS, 1.67 mM Ca and 15 µg/ml peptide. Prior to the experiments, the pH of concentrated 10×PBS was adjusted such that upon mixing, the pH of the final mineralization solution was 7.8. The TEM grids coated with reconstituted collagen fibrils were floated on 50 µL droplets of the mineralization solution at 100% humidity for 16 hours at 37° C.

Transmission Electron Microscopy (TEM)

TEM and selected area electron diffraction (SAED) studies were conducted using JEOL 1210 operated at 100 kV. The micrographs were recorded using an AMT CCD camera (AMT, Danvers, Mass.). An aluminum-coated TEM grid (EMS Hatfield, Pa.) was used as a standard for the calibration of SAED patterns for d-spacing calculations. The micrographs were analyzed using an ImageJ 1.38 software package (Bethesda, Md.).

Results

Peptide Design

A 3 Ser-Ser-Asp ($SSD_3$), a motif which comprises the major portion of DPP, was selected as a basis for a model peptide as shown in FIG. 1. The $SSD_3$ motif was flanked on the C-terminal end by a DEG-CK2 recognition motif and on the N-terminal side with DEDE-CK1 recognition motif indicated by SEQ NO. 1. Three N-terminal arginines (R) were added to create a cluster of positive charges at the N-terminus indicated by SEQ NO. 2. This addition counterbalanced the high negative charge of the rest of the peptide and therefore, eased the purification and handling of the peptide. The resulting peptide was named R-SSD3, indicated by SEQ NO. 2.

Phosphorylation

Figure 2:
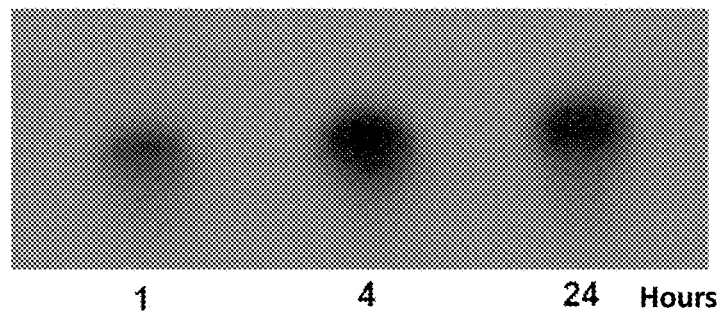
FIG. 2 is an autoradiogram which shows the invitro phosphorylation of R-SSD$_3$ by CK1, CK2 and CK1+CK2 at 1, 4 and 24 hours using $^{32}$P[γATP], in accordance with certain embodiments of the invention.
Figure 2:
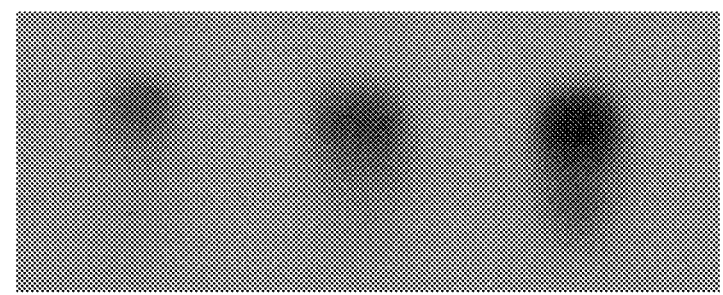
Figure 2:
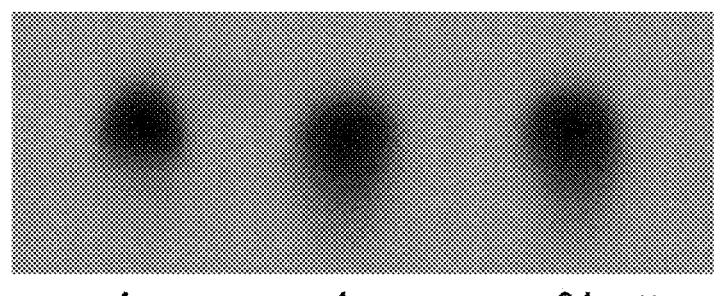

The phosphorylation studies were conducted in the presence of CK1, CK2 and the combination of these two enzymes. A visual analysis of the autoradiographs clearly indicated that in all three experiments, the degree of phosphorylation increased over 24 hours from the beginning of the reaction as shown in FIG. 2.

The extent of phosphorylation of the peptides was assessed using scintillation counter quantification. Based on the scintillation data, a number of phosphate groups per peptide molecule in all three experiments after 1 hour, 4 hours and 24 hours of incubation were calculated (as shown in Table 1). The results of the phosphorylation analysis showed that after one hour, a very small fraction of serines, between 0.1 and 2% were phosphorylated. At this stage, the degree of phosphorylation in the presence of CK1 was significantly lower than in the presence of combined CK1+CK2 ($p=0.018$).

Figure 3:
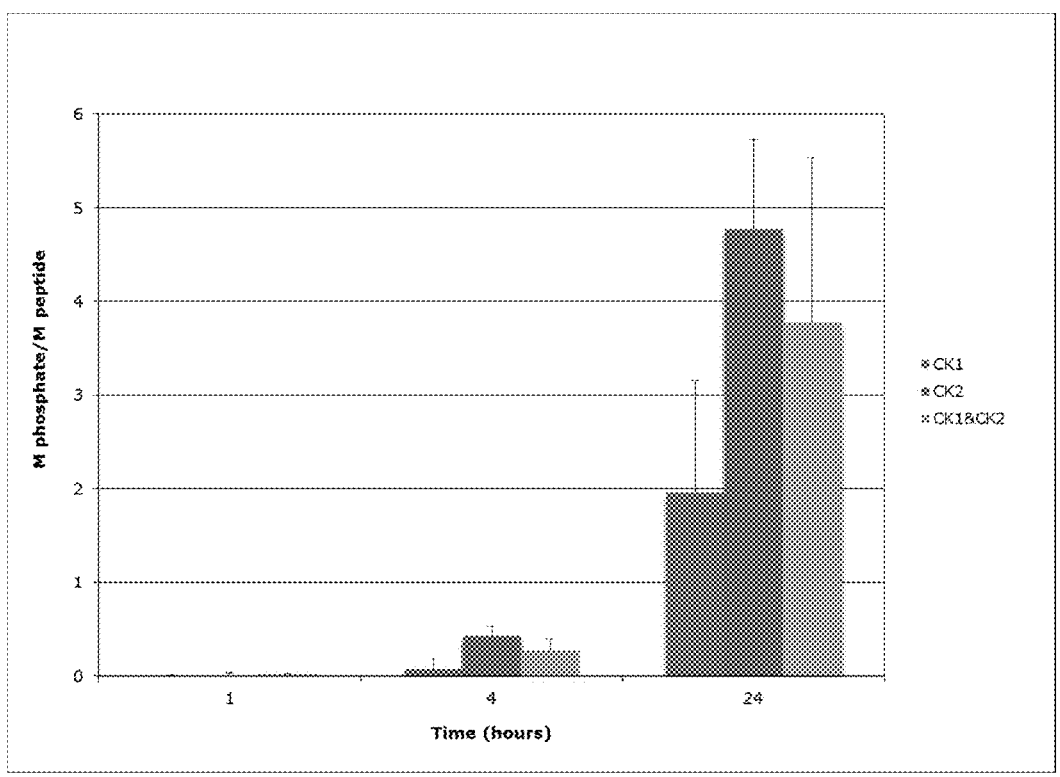
FIG. 3 is a bar graph which shows the extent of peptide phosphorylation by CK1 (blue bar), CK2 (red bar) and CK1+CK2 (green bar) of quantitative analysis of $^{32}$P[γATP] incorporation per mole of R-SSD3 peptides at 1, 4 and 24 hours, in accordance with certain embodiments of the invention.

At the same time, no significant differences in the degree of phosphorylation between CK1 and CK2 groups were observed (as shown in Table 2). Four hours into the reaction, the degree of phosphorylation had slightly, but statistically significantly increased with 2 to 6% of all serines phosphorylated. See FIG. 3. In all experiments, the difference in the degree of phosphorylation between one and four hour time points was statistically significant (Table 2). At the four hour time point, the degree of phosphorylation was significantly higher in the reaction in the presence of CK2 or a combination of CK1+CK2, than with CK1 alone (Table 2). The degree of phosphorylation between CK2 and CK1+CK2 groups was not statistically different (Table 2). By 24 hours, the peptides in all groups had attained a significant degree of phosphorylation with an average of 1.8 phosphates (30% of all serines) per peptide in the CK1 group, 4.4 phosphates (73% of all serines) in the CK2 group, and 3.5 phosphates (58% of all serines) in CK1+CK2 group. As in the four hour samples, the degree of phosphorylation in the presence of CK1 was significantly less than in the two other groups, while no significant differences were observed between the CK2 and CK1+CK2 groups (Table 1, Table 2).

TABLE 1

Phosphorylation Kinetics Based on Scintillation Analysis
The values in the Table 1 represent an average number of phosphates per peptide; standard deviation is given in parenthesis.

|  | 1 hour | 4 hours | 24 hours |
| --- | --- | --- | --- |
| CK1 | 0.006 (0.002) | 0.139 (0.103) | 1.778 (1.196) |
| CK2 | 0.0148 (0.015) | 0.435 (0.099) | 4.354 (0.957) |
| CK1 and CK2 | 0.0191 (0.007) | 0.343 (0.124) | 3.4555 (1.755) |

TABLE 2

T-Test of $RDSS_3$ Phosphorylation Kinetics with Different Kinases
The numbers in the table represent p-values;
P-values equal to or less than 0.05 are in bold.

|  | CK1 1 h | CK1 4 h | CK1 24 h | CK2 1 h | CK2 4 h | CK2 24 h | CK1/2 1 h | CK1/2 4 h | CK1/2 24 h |
| --- | --- | --- | --- | --- | --- | --- | --- | --- | --- |
| CK1 1 h |  | 0.045 | 0.03 | 0.179 |  |  | 0.018 |  |  |
| CK1 4 h |  |  | 0.038 |  | 0.011 |  |  | 0.046 |  |
| CK1 24 h |  |  |  |  |  | 0.022 |  |  | 0.12 |
| CK2 1 h |  |  |  |  | 0.011 | 0.009 | 0.34 |  |  |
| CK2 4 h |  |  |  |  |  | 0.002 |  | 0.187 |  |
| CK2 24 h |  |  |  |  |  |  |  |  | 0.24 |
| CK1/2 1 h |  |  |  |  |  |  |  | 0.005 | 0.014 |
| CK1/2 4 h |  |  |  |  |  |  |  |  | 0.019 |

Overall, the data indicated that CK2 phosphorylated the peptide at a significantly higher rate than CK1 and that addition of CK1 to CK2 did not affect the phosphorylation rate. Furthermore, the results indicated that multiple phosphorylation of the synthetic peptide could be achieved post-synthetically, demonstrating the feasibility of using of this technique for manufacturing peptides with multiple phosphorylation sites.

Figure 4:
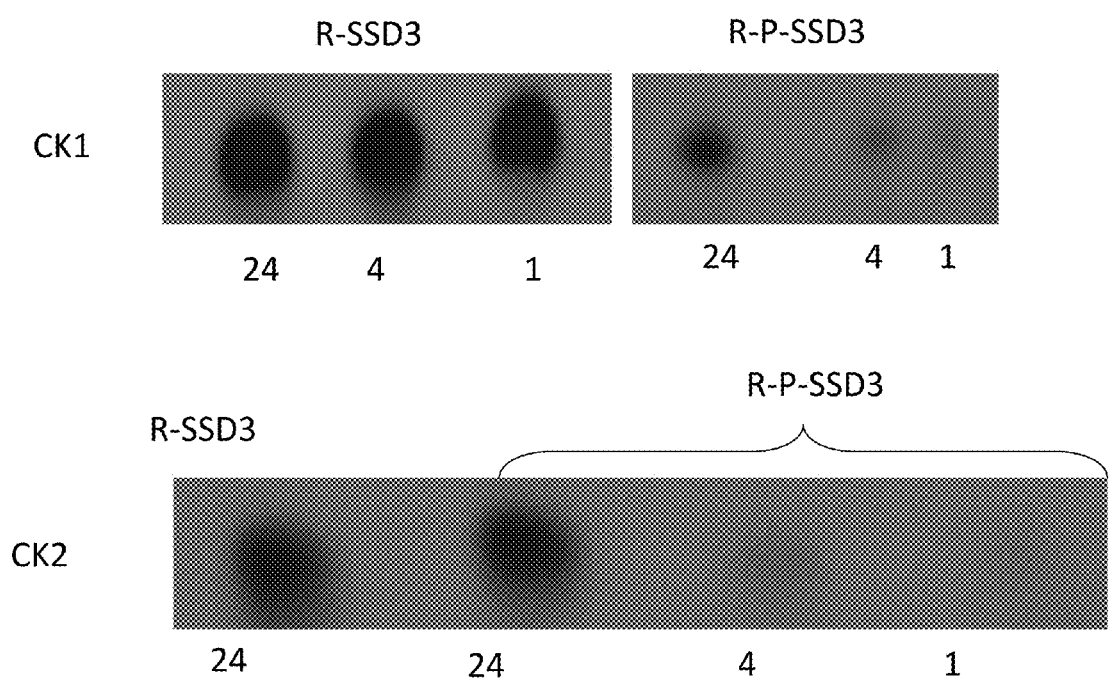
FIG. 4 is an autoradiogram which shows the in vitro phosphorylation of R-SSD$_3$ compared to R-P-SSD$_3$ where the CK1 site was modified, in accordance with certain embodiments of the invention.
Figure 5A:
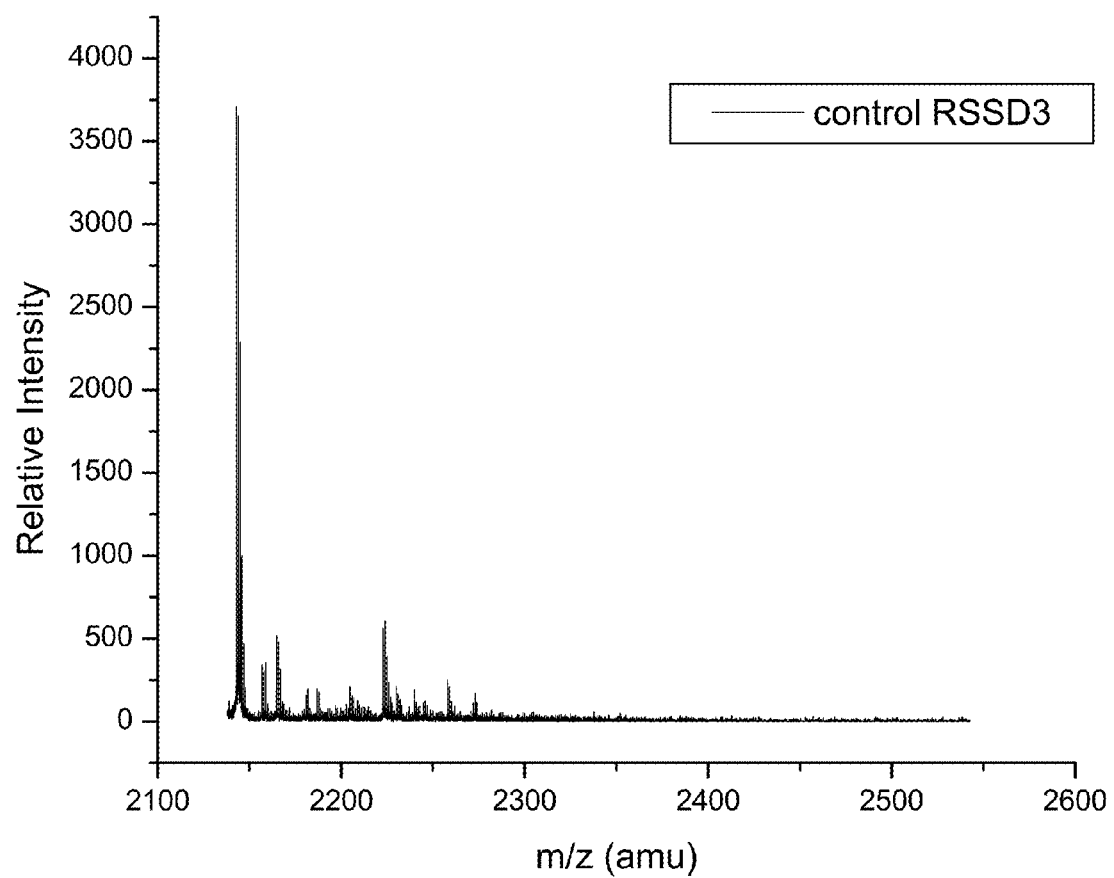
FIGS. 5A, 5B, 5C and 5D are mass spectrometry identifications of phosphates incorporated onto R-SSD$_3$ at one hour, in accordance with certain embodiments of the invention.
Figure 5B:
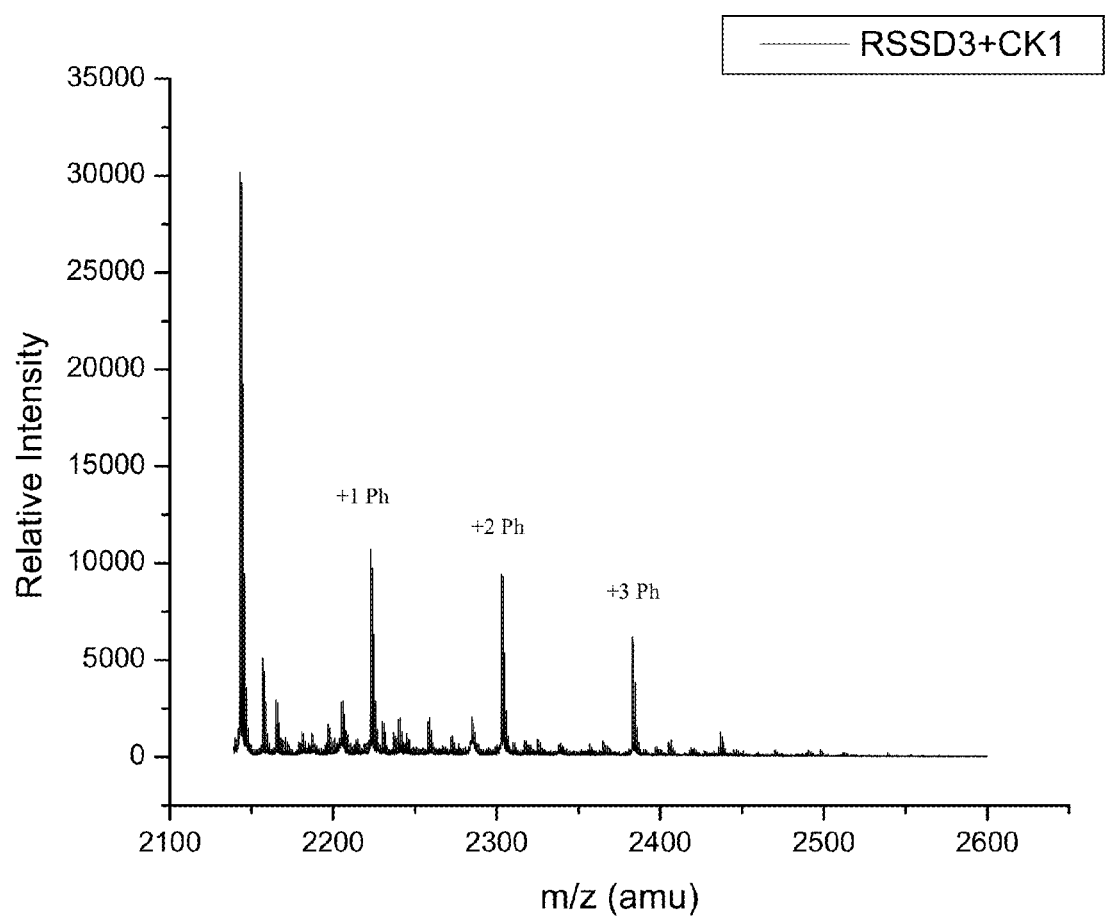
Figure 5C:
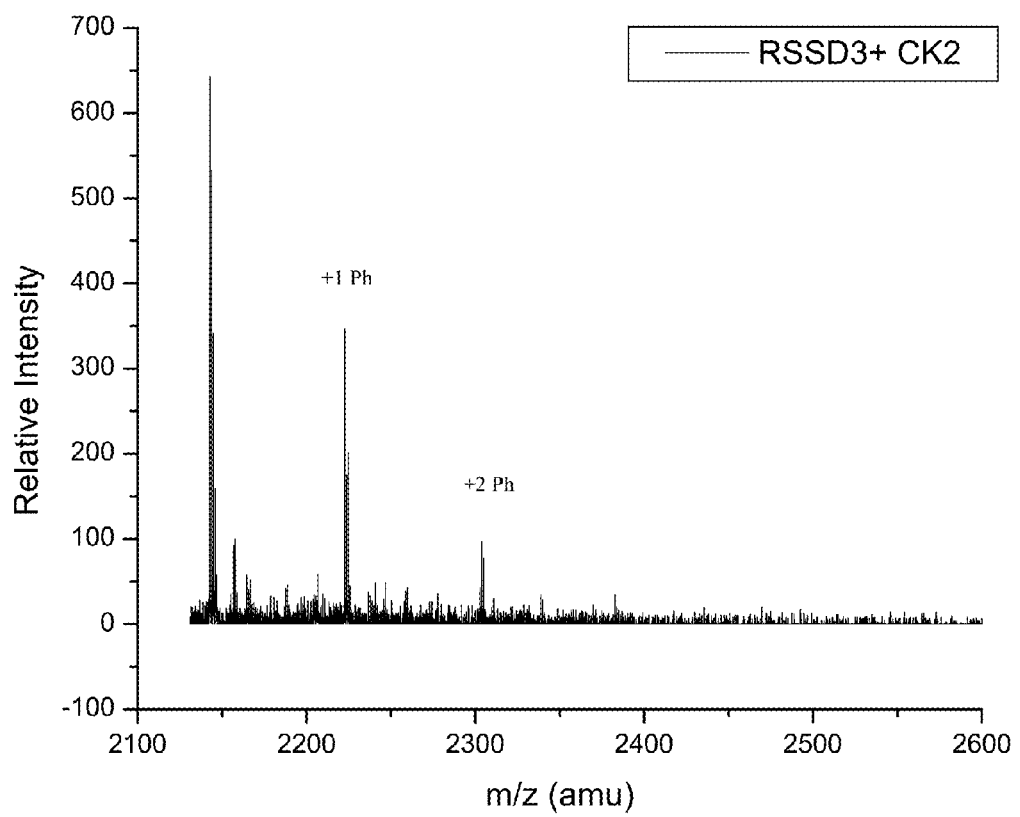
Figure 5D:
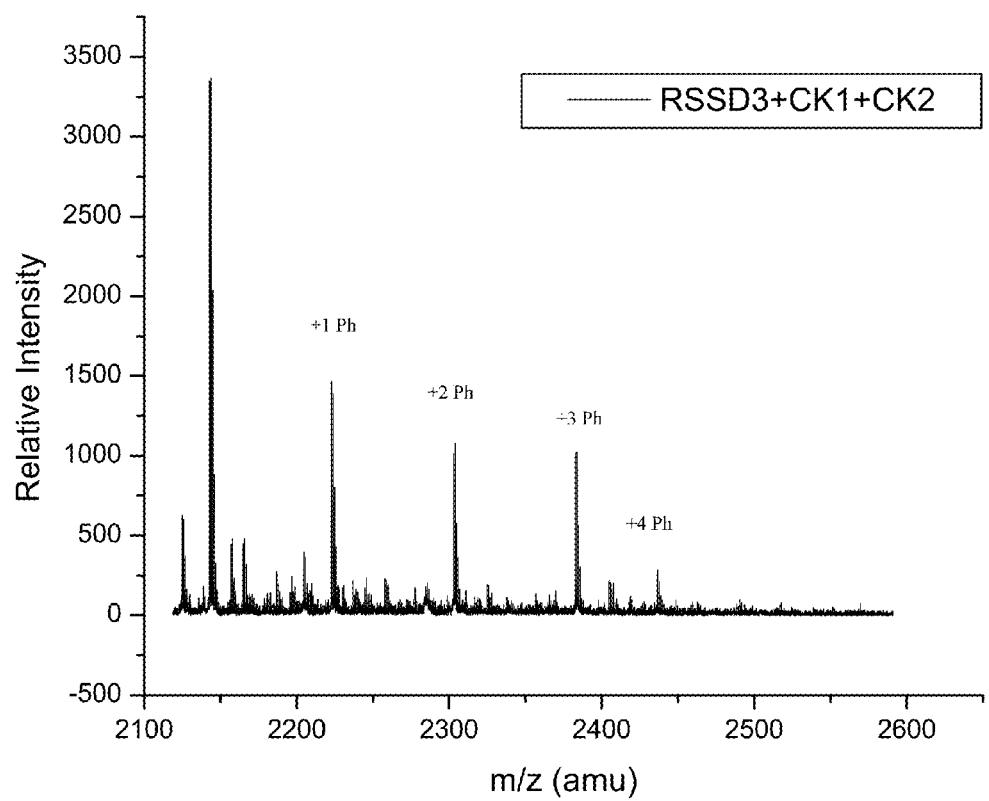

To further test the hypothesis that DPP phosphorylation is hierarchical, a modified peptide with a proline residue was designed to disturb the first recognition motif of CK1. In phosphorylation assays, a significant decrease in the degree of phosphorylation by CK1 of the modified R-P-SSD$_3$ peptide was observed compared to that of the original peptide as shown in FIG. 4. In contrast, this modification did not alter the degree of CK2 phosphorylation as shown in FIG. 4. These data indicated that CK1 phosphorylation is hierarchical, e.g., the CKI recognition motif was disturbed near a critically-placed serine and then, the overall phosphorylation of the peptide was dramatically reduced.

Mass Spectrometry (MS)

To quantify the number of phosphorylated serines, MS analysis revealed that the maximum number of phosphates incorporated onto the R-SSD$_3$ peptide indicated by SEQ NO. 2 was four out of six possible, when the in vitro phosphorylation of the peptide was carried out for one hour with a mixture of CK1 and CK2, as shown in FIGS. 5A, 5B, 5C and 5D.

Mineralization of Collagen Fibrils

Figures 6A, 6B, 6C:
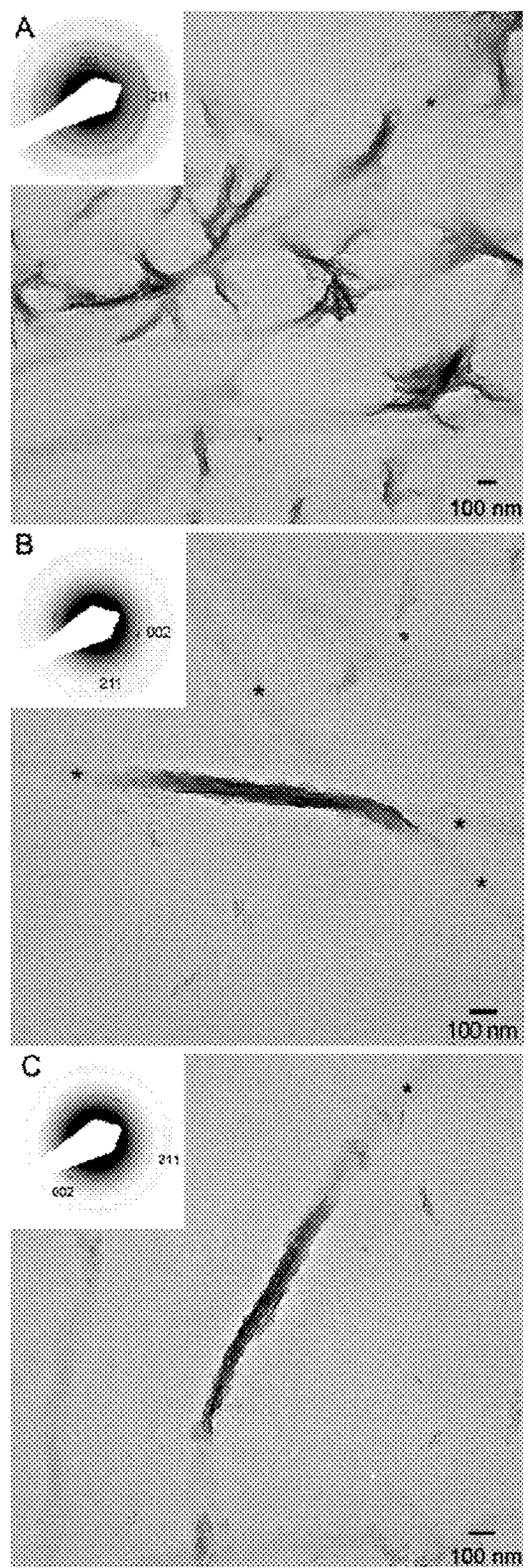
FIGS. 6A, 6B and 6C are TEM micrographs of collagen mineralization in the presence of nonphosphorylated R-SSD₃ (A) and phosphorylated R-SSD₃ (B, C) wherein the insets contain diffraction patterns from corresponding bright field images, in accordance with certain embodiments of the invention.

When reconstituted collagen fibrils were mineralized in the presence of nonphosphorylated R-SSD$_3$, indicated by SEQ NO. 2, indicated that randomly oriented crystals formed throughout the grid. No preferential co-localization and co-orientation of these crystals with the fibrils was observed as shown in FIG. 6A. In contrast, in the presence of the phosphorylated peptides, organized mineralization of collagen fibrils was observed as shown in FIGS. 6B and 6C. These mineralized collagen fibrils contained bundles of apatitic crystallites. Electron diffraction analysis confirmed that the mineral crystals had lattice parameters of hydroxyapatite and their optical c-axes were aligned with the axes of the fibrils. These structural features and alignments are exhibited by the mineralized collagen fibrils of bone and dentin. Almost no mineral crystals were observed outside of the collagen fibrils which indicated that R-SSD$_3$ indicated by SEQ NO. 2 suppressed mineral nucleation outside of the collagen fibrils. Furthermore, the diameters of mineralized and nonmineralized portions of the fibrils were of the same size, which suggested that the mineral was formed intrafibrillarly. These attributes of collagen mineralization in the presence of phosphorylated R-SSD$_3$ indicated by SEQ NO. 2 are similar to what had been observed in experiments with phosphorylated DPP, which suggests similarities in the mechanisms of regulation of mineralization by DPP and its model peptide R-SSD$_3$, indicated by SEQ NO. 2.

Phosphorylation

CK 1 and 2 can phosphorylate multiple phosphorylation sites in the R-SSD$_3$ indicated by SEQ NO. 2 synthetic peptide, modeled after motifs in the highly-phosphorylated, noncollagenous protein DPP. CK 1 and 2 phosphorylate this protein in vivo. CK2 having the higher phosphorylation potential was in accordance with data from in vivo studies showing that CK2 is essential for the phosphorylation of DPP. Furthermore, it has been demonstrated that high phosphorylation levels in synthetic peptides can be achieved using the post-synthesis phosphorylation approach.

Figure 7:
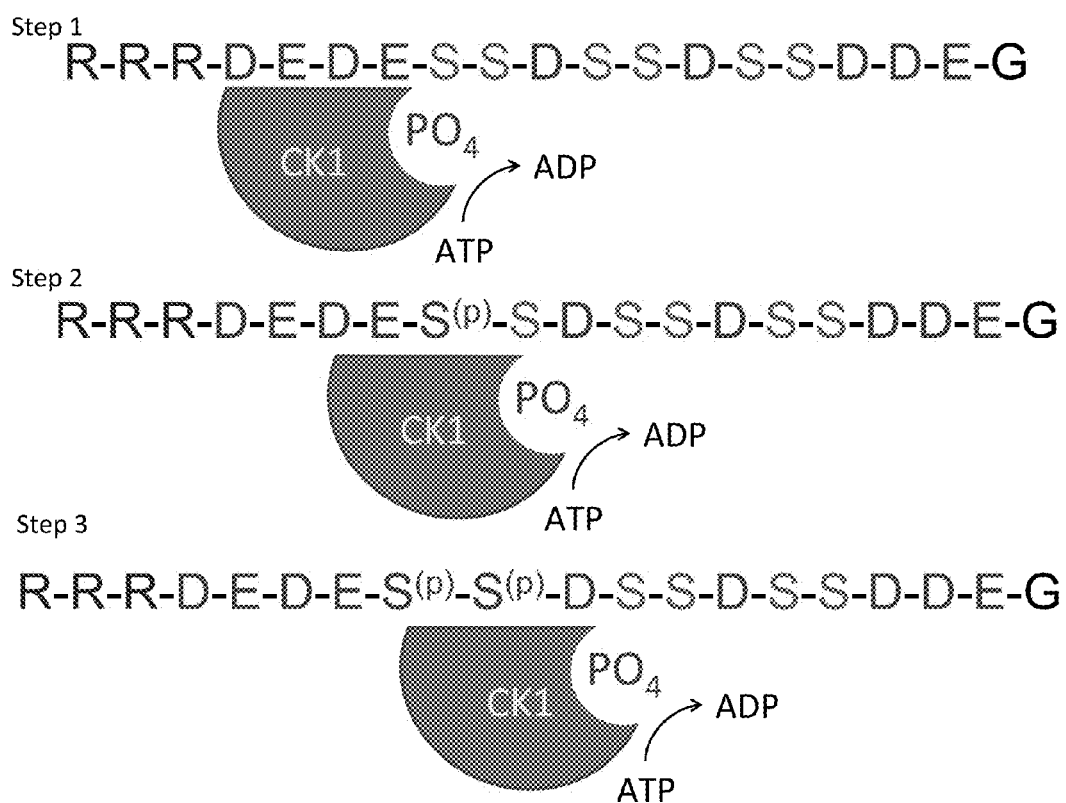
FIG. 7 is a schematic which shows CK1 hierarchical phosphorylation, in accordance with certain embodiments of the invention.

The results of the phosphorylation experiments with modified peptide suggested that phosphorylation of R-SSD3 peptides indicated by SEQ NO. 2 occurred via a chain or hierarchical mechanism. Numerous CK recognition sites have been described in the literature that share a common characteristic, namely, a stretch of negatively-charged amino acids. Thus, it was proposed that in the case of DPP, phosphorylation of serine next to the kinase recognition site leads to the formation of negatively charged phosphoserine. This phosphoserine becomes a part of a CK recognition site, allowing for the subsequent phosphorylation of additional serines as shown in FIG. 7. The results of the phosphorylation experiments with R-SSD$_3$ indicated by SEQ NO. 2 demonstrated that both CK1 and CK2 could phosphorylate multiple serines in (DSS)n sequence. Furthermore, in the experiments, the amount of phosphorylation significantly decreased which indicated that the phosphorylation by CK1 progressed hierarchically from the N-terminus towards the C-terminus.

Mineralization

The mineralization experiments with phosphorylated R-SSD$_3$ indicated by SEQ NO. 2 demonstrated the same trends observed in the experiments using full-length DPP molecules indicating that phosphorylated DSS repeats were involved in the regulation of mineralization by DPP. In both cases, the phosphorylated molecules induced organized mineralization of collagen fibrils, structurally similar to the mineralized collagen fibrils of bone and dentin, and nonphosphorylated molecules did not have any significant effect on collagen mineralization. In the presence of R-SSD$_3$, indicated by SEQ NO. 2, crystal formation outside of the collagen fibrils was inhibited and collagen mineralization occurred intrafibrillarly. This suggested that the mechanism of mineralization by highly acidic proteins such as DPP and poly-L-Asp share some similarities. In a recent cryoEM study in the art, poly-L-Asp was used as a model for acidic noncollagenous proteins and it was shown that this peptide could stabilize calcium phosphate prenucleation clusters and prevent their aggregation into amorphous and crystalline mineral phases. It was further demonstrated that negatively charged complexes of poly-L-Asp and prenucleation clusters entered the collagen fibrils in the gap regions attracted by a concentration of positive charge where the prenucleation clusters transformed into apatitic crystallites. Based on the similarities of the mineralization reaction products between poly-L-Asp and phosphorylated DPP and R-DSS$_3$, indicated by SEQ NO. 2, it is believed that these molecules regulate collagen mineralization in a similar manner. Similarly-organized mineralized collagen fibrils have been achieved using synthetic additives such as polyphosphate and polyacrylate. Furthermore, it is contemplated that such strategies for biomimetic remineralization of dental tissues using synthetic additives may be successful. New bioinspired peptide designs will result in the development of strategies for highly controlled biomimetic peptide-based mineralized tissue regeneration, and the development of novel nanocomposite materials.

The results showed that nanocomposite mineralized fibrils which mimick mineralized fibrils of bone and dentin can be synthesized using phosphorylated peptides (R-SSD$_3$ indicated by SEQ NO. 2) modeled after the major NCP of dentin DPP. Additionally, the phosphorylation of R-SSD$_3$ peptides indicated by SEQ NO. 2 at multiple serine sites can be achieved. Highly phosphorylated peptides can be manufactured via post-synthesis phosphorylation. The data obtained provides support for the hypothesis of hierarchical phosphorylation of the NCPs.

Example 2—Tissue Culture in the Presence of Biomimetic DSS3 and DSS5 Peptides

Figure 8A:
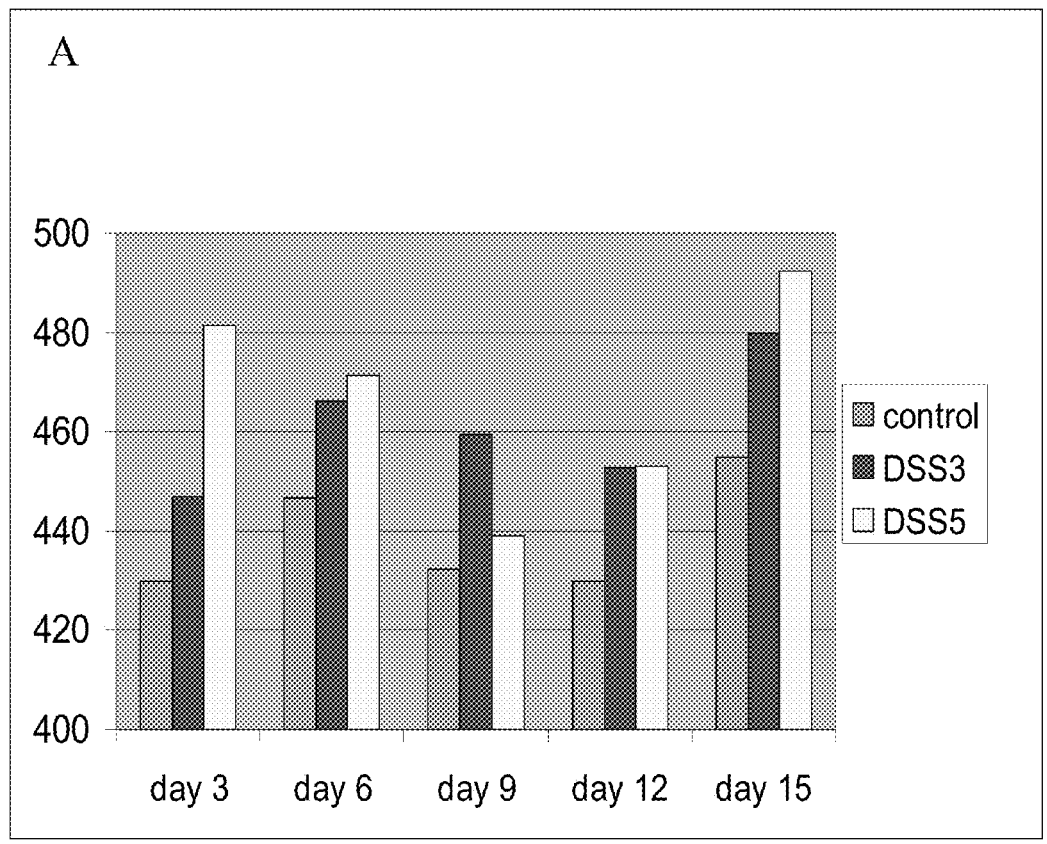
FIGS. 8A and 8B are plots of the concentration of ALP in cell cultures over a 15-day period in non-osteogenic media and osteogenic media, respectively, in accordance with certain embodiments of the invention.
Figure 8B:
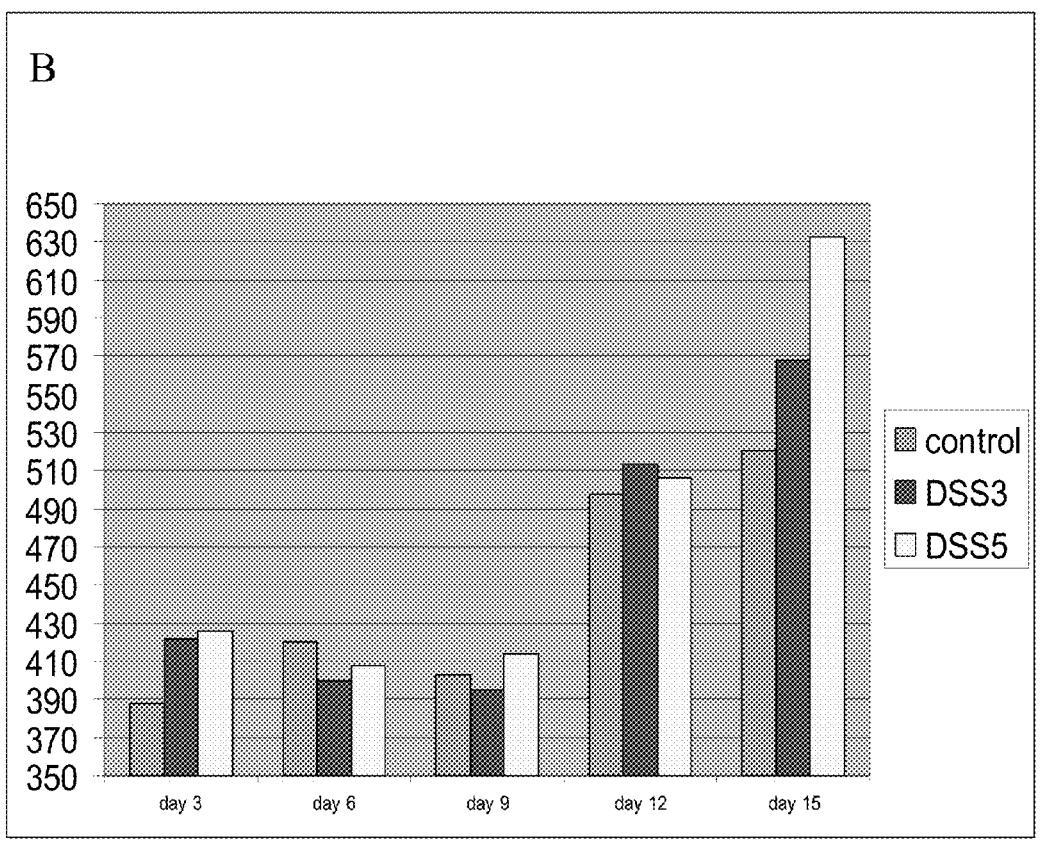

DSS$_3$ and DSS$_5$ were dissolved in poly-L-lysine solution in DDW at the concentration of 10 μm/ml followed by coating of the polystyrene cell culture six well plates. The plates coated with poly-L-lysine only were used as a control. MC3T3 cells were seeded into the plates in triplicate and cultured for 15 days in non-osteogenic and osteogenic α-MEM tissue culture media. Alkaline phosphatase activity was used as a measure of osteogenic differentiation of the cells. In the osteogenic medium ALP concentrations were higher than in the controls. These differences were not statistically significant. However, there was observed between the controls and peptide treatments under non-osteogenic conditions in both $DSS_3$ and $DSS_5$ treated groups a statistically significant increase in ALP concentration ($p \ll 0.05$) as shown in FIGS. 8A and 8B. FIG. 8A shows the concentrations of ALP in the cell cultures over a 15-day period in the nonosteogenic media and FIG. 8B shows the concentrations of ALP in the cell cultures over a 15-day period in the osteogenic media. These results suggested that the biomimetic peptides synthesized were not cytotoxic and had osteogenic potential.

Example 3—In Vivo Bone Regeneration

Figure 9:
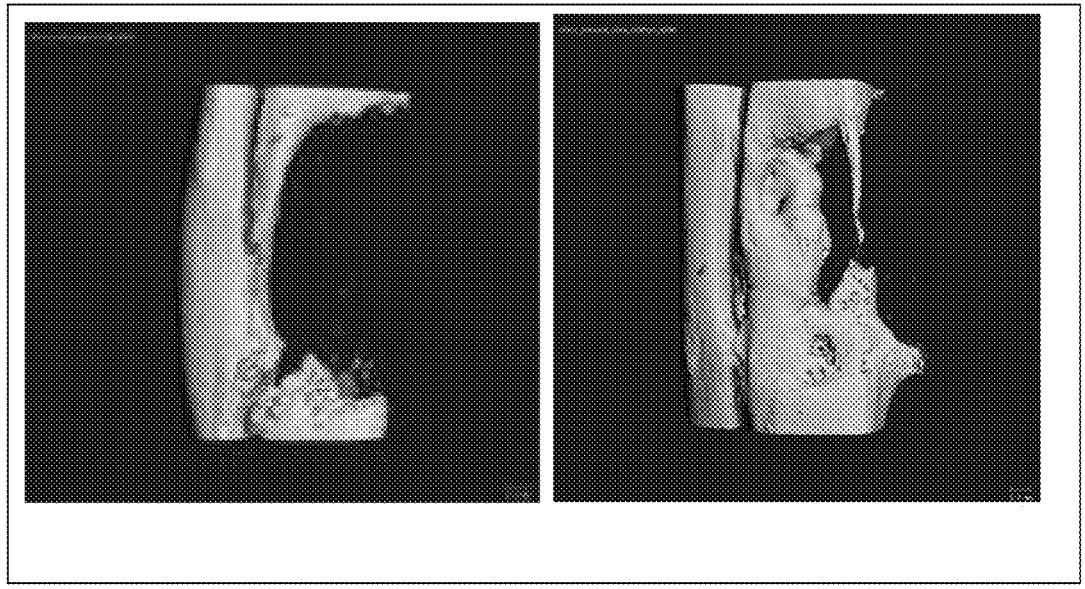
FIG. 9 provides MicroCT scans showing reconstruction of a rabbit ulna critical size defect including no implant and an implant of collagen carrier containing R-SSD₃ peptide, in accordance with certain embodiments of the invention.
Figures 10A, 10B:
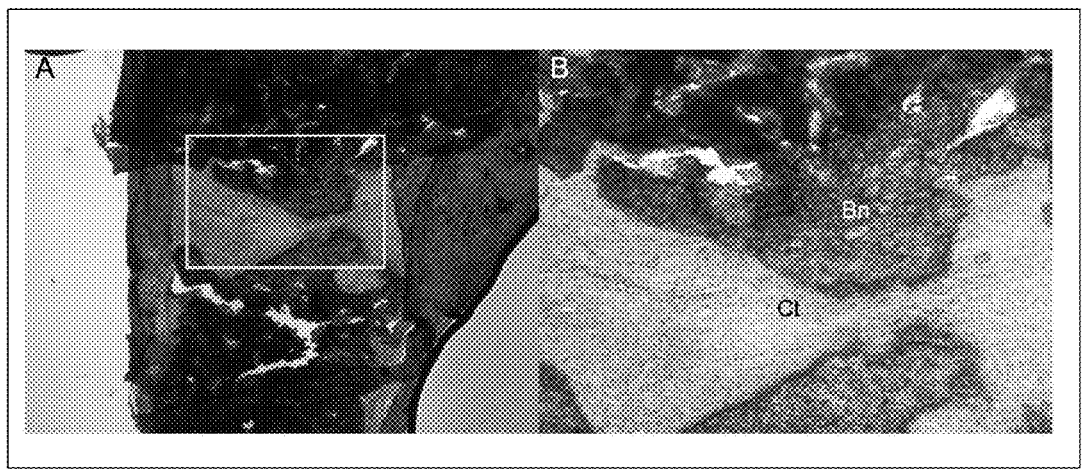
FIG. 10A is a low magnification image of H&E stained nondecalcified sections of new regenerating ulnar bone and FIG. 10B is a close-up image of the area identified by a rectangle in FIG. 10A, in accordance with certain embodiments of the invention.

A collagen scaffold containing R-$SSD_5$ indicated by SEQ NO. 2 peptide was implanted into a critical size defect in a rabbit ulna model. After 8 weeks, significant bone re-growth was observed as shown in FIG. 9. FIG. 9 shows a MicroCT reconstruction of the rabbit ulna critical size defect implanted with collagen carrier containing R-$SSD_5$ indicated by SEQ NO. 2 peptide eight weeks after the surgery. As demonstrated in FIG. 9 in the right panel, significant bone re-growth was observed as compared to the control with no implant shown in the left panel. The results suggested that the peptide had osteogenic potential. FIG. 10A is a low-magnification image and FIG. 10B is a close up of the area in FIG. 10A identified by a rectangle, of H&E stained nondecalcified sections of the regenerating ulnar bone eight weeks after the surgery. FIG. 10A demonstrates almost complete bridging of the critical size defect by bone. The presence of cartilage between two newly formed bone regions indicated that the bone formation occurred via endochondral pathway as shown in FIG. 10B. Overall, the data strongly suggested that R-$SSD_5$ indicated by SEQ NO. 2 had an osteogenic potential and also demonstrated its potential for bone tissue repair.

The invention claimed is:

1. A peptide selected from the group consisting of: RRRGDEDE(SSD)$_n$DEG, wherein n is an integer selected from 3 and 5, indicated by SEQ NO. 3.

2. The peptide of claim 1, consisting of: RRRGDEDESSDSSDSSDDEG, indicated by SEQ NO. 3.

3. A mineralized collagen fibril which comprises collagen fibrils, organized mineral crystals and the peptide of claim 1 to promote the organized mineralization of collagen fibrils.

4. A biomimetic composite which comprises collagen fibrils, organized mineral crystals and the peptide of claim 1 to promote the organized mineralization of collagen fibrils.

5. A process for preparing a phosphorylated peptide, comprising:

forming the peptide of claim 1; and
phosphorylating multiple amino acid sites of the peptide of claim 1.

6. The process of claim 5, wherein the phosphorylating of the peptide employs casein kinases.

7. The process of claim 6, wherein up to 80% of serines in the peptide are phosphorylated by casein kinases.

8. The process of claim 6, wherein the phosphorylating employs CK1, CK2 or a combination thereof.

9. The process of claim 5, wherein ATP is a source of phosphate.

10. The peptide of claim 1, wherein for the RRRGDEDE (SSD)$_n$DEG peptide wherein n is an integer selected from 3 and 5, a DEG sequence and a DEDE sequence, each provide a first recognition site and a second recognition site, respectively, to phosphorylate a (SSD)n sequence.

* * * * *

UNITED STATES PATENT AND TRADEMARK OFFICE
CERTIFICATE OF CORRECTION

PATENT NO. : 9,937,279 B2
APPLICATION NO. : 14/943479
DATED : April 10, 2018
INVENTOR(S) : Elia Beniash et al.

It is certified that error appears in the above-identified patent and that said Letters Patent is hereby corrected as shown below:

In the Specification

Column 1, Lines 16-19:
"This invention was made with government support under DE 106703 and DE 016123 awarded by the National Institutes of Health (NIH). The government has certain rights in the invention."

Should read:
--GOVERNMENT SUPPORT
This invention was made with government support under grant numbers DE106703 and DE016123 awarded by the National Institutes of Health and grant number EEC0812348 awarded by the National Science Foundation. The government has certain rights in the invention.--

Signed and Sealed this
Third Day of September, 2019

Andrei Iancu
*Director of the United States Patent and Trademark Office*